(12) United States Patent
Soletti et al.

(10) Patent No.: US 9,155,610 B2
(45) Date of Patent: Oct. 13, 2015

(54) SYSTEM AND ATRAUMATIC MANDREL FOR CREATING GRAFT DEVICES

(71) Applicant: Neograft Technologies, Inc., Taunton, MA (US)

(72) Inventors: Lorenzo Soletti, Pittsburgh, PA (US); Mohammed S. El-Kurdi, Mansfield, MA (US); Jon McGrath, Duxbury, MA (US); J. Christopher Flaherty, Topsfield, MA (US)

(73) Assignee: NEOGRAFT TECHNOLOGIES, INC., Taunton, MA (US)

( * ) Notice: Subject to any disclaimer, the term of this patent is extended or adjusted under 35 U.S.C. 154(b) by 0 days.

(21) Appl. No.: 14/364,989

(22) PCT Filed: Dec. 12, 2012

(86) PCT No.: PCT/US2012/069102
§ 371 (c)(1),
(2) Date: Jun. 12, 2014

(87) PCT Pub. No.: WO2013/090337
PCT Pub. Date: Jun. 20, 2013

(65) Prior Publication Data
US 2014/0332164 A1 Nov. 13, 2014

Related U.S. Application Data

(60) Provisional application No. 61/569,941, filed on Dec. 13, 2011.

(51) Int. Cl.
*B29C 53/58* (2006.01)
*B29C 65/00* (2006.01)
(Continued)

(52) U.S. Cl.
CPC . *A61F 2/062* (2013.01); *A61F 2/06* (2013.01); *D01D 5/0084* (2013.01); *D04H 1/728* (2013.01);
(Continued)

(58) Field of Classification Search
CPC ............. A61F 2/06; A61F 2/062; A61F 2/07; A61F 2/82; A61F 2/86; A61F 2/88; A61F 2/90; A61F 2210/0076; A61F 2240/00; A61F 2240/001; A61F 2220/005; A61L 27/507; D04H 1/728; D04H 1/76; D01D 5/0076; D01D 5/0084; A61B 2017/00526; B29C 65/00; B29C 65/48; B29C 66/1122; B29C 66/5221; B29C 67/0018; B32B 1/08
USPC ........... 156/60, 143, 148, 149, 150, 166, 167, 156/169, 172, 242, 244.11, 272.2, 273.1, 156/274.4, 274.6, 274.8, 275.7, 293, 294, 156/297, 349, 379.6, 379.8, 380.2, 380.3, 156/381, 391, 423, 425, 426, 427, 538, 156/578; 600/36; 623/1.13, 1.14, 1.49, 623/1.39, 1.41, 1.44, 1.46, 1.5, 1.15, 1.16, 623/1.21, 1.22, 1.32, 1.51, 1.53, 901; 264/465, 466; 424/422, 423; 425/174.8 R, 174.8 E
See application file for complete search history.

(56) References Cited

U.S. PATENT DOCUMENTS

| | | | |
|---|---|---|---|
| 4,955,899 | A | 9/1990 | Della Corna et al. |
| 5,662,700 | A | 9/1997 | Lazarus |

(Continued)

FOREIGN PATENT DOCUMENTS

| | | |
|---|---|---|
| EP | 0265176 | 4/1988 |
| WO | 2010042721 | 4/2010 |

(Continued)

OTHER PUBLICATIONS

Courtney et al., Design and analysis of tissue engineering scaffolds that mimic soft tissue mechanical anisotropy, Biomaterials, Mar. 2006, pp. 3631-3638, vol. 27, Issue 19, Elsevier Science, Netherlands. (8 pages).

(Continued)

*Primary Examiner* — Philip Tucker
*Assistant Examiner* — Brian R Slawski
(74) *Attorney, Agent, or Firm* — Wilson Sonsini Goodrich & Rosati P.C.

(57) ABSTRACT

In some aspects, a system for applying a fiber matrix on a tubular conduit is provided. The system can include a tubular conduit, a mandrel and a fiber matrix delivery assembly. The mandrel can comprise an elongate shaft and a rolling membrane configured to atraumatically engage the tubular conduit.

20 Claims, 9 Drawing Sheets

(51) Int. Cl.

| | |
|---|---|
| B32B 37/00 | (2006.01) |
| A61F 2/04 | (2013.01) |
| A61F 2/06 | (2013.01) |
| B29C 47/00 | (2006.01) |
| H05B 7/00 | (2006.01) |
| B27N 3/14 | (2006.01) |
| B29C 33/04 | (2006.01) |
| B29C 47/88 | (2006.01) |
| D04H 1/728 | (2012.01) |
| D01D 5/00 | (2006.01) |
| D04H 3/073 | (2012.01) |
| D04H 1/76 | (2012.01) |
| B29C 65/48 | (2006.01) |
| B32B 1/08 | (2006.01) |

(52) U.S. Cl.
CPC ............... *D04H 1/76* (2013.01); *D04H 3/073* (2013.01); *B29C 65/48* (2013.01); *B29C 66/5221* (2013.01); *B32B 1/08* (2013.01)

(56) References Cited

U.S. PATENT DOCUMENTS

| | | | |
|---|---|---|---|
| 6,036,724 | A | 3/2000 | Lentz et al. |
| 6,891,077 | B2 | 5/2005 | Rothwell et al. |
| 7,452,374 | B2 | 11/2008 | Hain et al. |
| 7,759,099 | B2 | 7/2010 | Wolf et al. |
| 7,759,120 | B2 | 7/2010 | Wolf et al. |
| 7,794,219 | B2 | 9/2010 | Dubson et al. |
| 7,998,188 | B2 | 8/2011 | Zilla et al. |
| 8,057,537 | B2 | 11/2011 | Zilla et al. |
| 8,172,746 | B2 | 5/2012 | Zilla et al. |
| 8,992,594 | B2 | 3/2015 | Soletti et al. |
| 2002/0042128 | A1 | 4/2002 | Bowlin et al. |
| 2002/0169499 | A1 | 11/2002 | Zilla et al. |
| 2004/0058887 | A1 | 3/2004 | Bowlin et al. |
| 2004/0094873 | A1 | 5/2004 | Dubson et al. |
| 2004/0146546 | A1 | 7/2004 | Gravett et al. |
| 2005/0085888 | A1 | 4/2005 | Andreas et al. |
| 2005/0203636 | A1 | 9/2005 | McFetridge |
| 2006/0041302 | A1* | 2/2006 | Malewicz .................... 623/1.11 |
| 2006/0085063 | A1 | 4/2006 | Shastri et al. |
| 2006/0204441 | A1 | 9/2006 | Atala et al. |
| 2006/0240061 | A1 | 10/2006 | Atala et al. |
| 2007/0293932 | A1 | 12/2007 | Zilla et al. |
| 2008/0208323 | A1 | 8/2008 | El-Kurdi et al. |
| 2009/0012607 | A1 | 1/2009 | Kim et al. |
| 2010/0160718 | A1 | 6/2010 | Villafana et al. |
| 2012/0116495 | A1 | 5/2012 | Zilla et al. |
| 2012/0330437 | A1 | 12/2012 | El-Kurdi et al. |

FOREIGN PATENT DOCUMENTS

| | | |
|---|---|---|
| WO | 2011082295 | 7/2011 |
| WO | WO 2011/084559 A2 | 7/2011 |
| WO | WO 2012/097229 A2 | 7/2012 |
| WO | WO 2012/109309 A2 | 8/2012 |

OTHER PUBLICATIONS

Deitzel et al., Controlled deposition of electrospun poly(ethylene oxide) fibers, Polymer, Sep. 2001, pp. 8163-8170, vol. 42, Issue 19, Elsevier Science, England. (8 pages).

Ducasse et al., Interposition Vein Cuff and Intimal Hyperplasia: An Experimental Study, Eur. J. Vasc. Endovasc. Surg., Jun. 2004, pp. 617-621, vol. 27, Issue 6, Elsevier, London. (5 pages).

Kohler et al., The effect of Rigid External Support on Vein Graft Adaptation to the Arterial Circulation, J. Vasc. Surg., Feb. 1989, pp. 277-285, vol. 9, Issue 2, Mosby-Elsevier, St. Louis, MD. (9 pages).

Kohler et al., Inhibition of Neointimal Hyperplasia in a Sheep Model of Dialysis Access Failure with the Bioabsorbable Vascular Wrap Paclitaxel-Eluting Mesh, J. Vasc. Surg., May 2007, pp. 1029-1038, vol. 45, Issue 5, Mosby-Elsevier, St. Louis, MO. (13 pages).

Moritz et al., A Method for Constricting Large Veins for Use in Arterial Vascular Reconstruction, Artificial Organs, Oct. 1990, pp. 394-398, vol. 14, Issue 5, Wiley-Blackwell, Cambridge, MA. (5 pages).

Stankus et al., Fabrication of Biodegradable Elastomeric Scaffolds with Sub-Micron Morphologies, J. Biomed. Mater Res. A., Sep. 2004, pp. 603-614, vol. 70, Issue 4, Wiley, Hoboken, NJ. (25 pages).

Stankus et al., Microintegrating Smooth Muscle Cells into a Biodegradable, Elastomeric Fiber Matrix, Biomaterials, Feb. 2006, pp. 735-744, vol. 27, Issue 5, Elsevier Sciences, Netherlands. (17 pages).

Stitzel et al., Controlled fabrication of a biological vascular substitute, Biomaterials, Aug. 2006, pp. 1088-1094, vol. 27, Issue 7, Elsevier Science, Netherlands. (7 pages).

Stooker et al., Perivenous application of fibrin glue reduces early injury to the human saphenous vein graft wall in an ex vivo model, European Journal of Cardio-thoracic Surgery, Feb. 2002, pp. 212-217, vol. 21, Issue 2, Elsevier Science, Germany. (6 pages).

Tai et al., Compliance Properties of Conduits Used in Vascular Reconstruction, Br. J. Surg., Nov. 2000, pp. 1516-1524, vol. 87, Issue 11, John Wiley & Sons, England. (9 pages).

Traver et al., New Generation Tissue Sealants and Hemostatic Agents: Innovative Urologic Applications, Reviews in Urology, Summer 2006 edition, pp. 104-111, vol. 8, Issue 3, RIU Publishers, Mercer Island, WA (USA). (8 pages).

Vijayan et al., External Supports and the Prevention of Neointima Formation in Vein Grafts, Eur. J. Vasc. Endovasc. Surg., Jul. 2002, pp. 13-22, vol. 24, Issue 1, Elsevier, London. (10 pages).

Vijayan et al., Long-Term Reduction of Medial and Intimal Thickening in Porcine Saphenous Vein Grafts with a Polyglactin Biodegradable External Sheath, J. Vasc. Surg., Nov. 2004, pp. 1011-1019, vol. 40, Issue 5, Mosby-Elsevier, St. Louis, MO. (9 pages).

Ayres, et al. Modulation of anisotropy in electrospun tissue-engineering scaffolds: Analysis of fiber alignment by the fast Fourier transform. Biomaterials 27 (2006) 5524-5534.

Ben-Gal, et al. Expandable external support device to improve saphenous vein graft patency after cabg. J Cardiothorac Surg 2013; 8:122.

Chakrabarty, S. Fibrin solubilizing properties of certain anionic and cationic detergents. Thrombosis research 55.4 (1989): 511-519.

Deitzel, et al. The effect of processing variable on the morphology of electrospun nanofibers and textiles. Polymer 42 (2001): 261-272.

Hermans, et al. Fibrin: structure and interactions. Seminars in thrombosis and hemostasis. vol. 8. No. 1. 1982.

International preliminary report on patentability and written opinion dated Mar. 29, 2013 for PCT Application No. US2012/069102.

International search report and written opinion dated Mar. 29, 2013 for PCT Application No. US2012/069102.

Izzat, et al. Influence of external stent size on early medial and neointimal thickening in a pig model of saphenous vein bypass graftin. Circulation 1996; 94:1741-5.

Jankowski-Bell, et al. Histology of Blood Vessels—www2. victoriacollege.edu/dept/bio/Belltutorials/Histology%20Tutorial/ Blood%20Vess els/Histology_of_Blood_Vessels.html.

Jeremy, et al. A bioabsorbable (polyglactin), nonrestrictive, external sheath inhibits porcine saphenous vein graft thickening. J Thorac Cardiovasc Surg. 2004;127(6): 1766-72.

Levorson, et al. Fabrication and characterization of multiscale electrospun scaffolds for cartilage regeneration. Biomed Mater 2013;8:014103. doi:10.1088/1748-6041/8/1/014103.

McManus, et al. Electrospun fibrinogen: feasibility as a tissue engineering scaffold in a rat cell culture model. Journal of Biomedical Materials Research Part A 81.2 (2007): 299-309.

Mcmanus, et al. Mechanical properties of electrospun fibrinogen structures. Acta Biomaterialia 2.1 (2006): 19-28.

Mehta, et al. External stenting reduces long-term medial and neointimal thickening and platelet derived growth factor expression in a pig model of arteriovenous bypass grafting. Nat Med. 1998;4(2): 235-9.

Morton, et al. Electrospun fibrin nanofibers for the use in tissue engineering. Modification of fibrin to improve applications in regenerative medicine (2010): 81.

(56) References Cited

OTHER PUBLICATIONS

Mosesson, M.W. Fibrinogen and fibrin structure and functions. Journal of Thrombosis and Haemostasis 3.8 (2005): 1894-1904.

Parsonnet, et al. New stent for support of veins in arterial grafts. Arch Surg. 1963;87: 696702.

Perumcherry, et al. A Novel Method for the Fabrication of Fibrin-Based Electrospun Nanofibrous Scaffold for Tissue-Engineering Applications*. Tissue Engineering Part C: Methods 17.11 (2011): 1121-1130.

Sell, et al. Cross-linking methods of electrospun fibrinogen scaffolds for tissue engineering applications. Biomedical Materials 3.4 (2008): 045001.

Sreerekha, et al. Fabrication of fibrin based electrospun multiscale composite scaffold for tissue engineering applications. Journal of biomedical nanotechnology 9.5 (2013): 790-800.

Wan, et al. Differential, time-dependent effects of perivenous application of fibrin glue on medial thickening in porcine saphenous vein grafts. European Journal of Cardiothoracic Surgery, 29, (2006): 742-747.

Weisel, et al. Computer modeling of fibrin polymerization kinetics correlated with electron microscope and turbidity observations: clot structure and assembly are kinetically controlled. Biophysical journal 63.1 (1992): 111.

Weisel, et al. Mechanisms of fibrin polymerization and clinical implications. Blood 121.10 (2013): 1712-1719.

Wnek, et al. Electrospinning of nanofiber fibrinogen structures. Nano Letters 3.2 (2003): 213-216.

Xu, et al. Electrospun Nanofiber Fabrication as Synthetic Extracellular Matrix and Its Potential for Vascular Tissue Engineering. Tissue Engineering, vol. 10, No. 7/8, 2004.

Yu, et al. Electrospinning, Encyclopedia of Polymer Science & Technology (2008) 1-20.

Zilla, et al. Constrictive external nitinol meshes inhibit vein graft intimal hyperplasia in nonhuman primates. The Journal of Thoracic and Cardiovascular Surgery 2008;136:717-725.

Zilla, et al. Utilization of shape memory in external vein-graft meshes allows extreme diameter constriction for suppressing intimal hyperplasia: A non-human primate study. J Vasc Surg 2009;49:1532-42.

* cited by examiner

FIG 2A
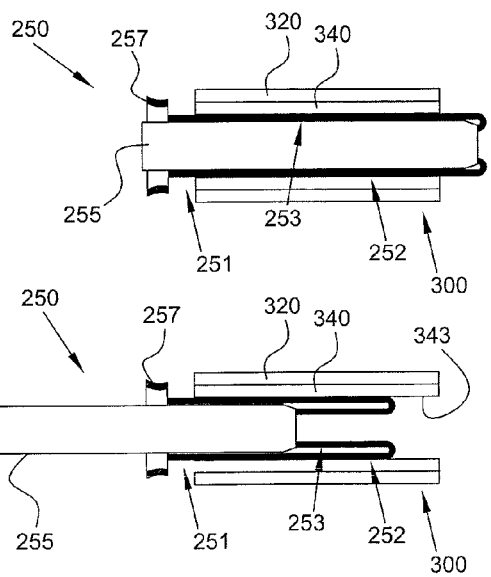
FIG 2B
FIG 2C
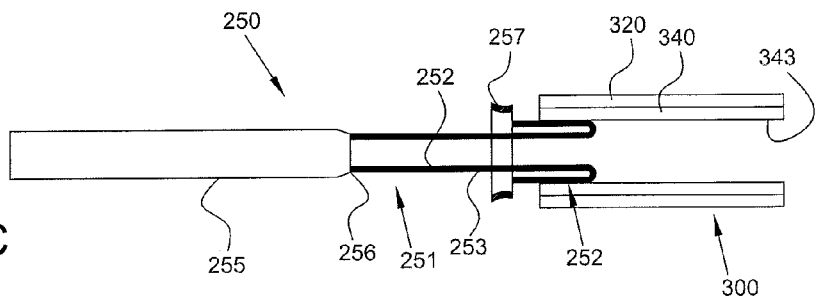
FIG 2D
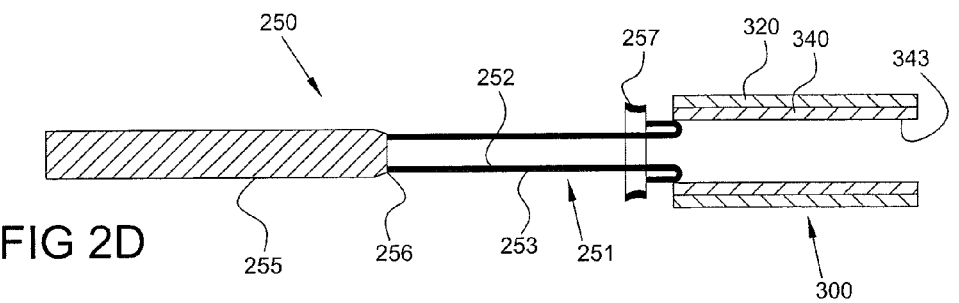

SYSTEM AND ATRAUMATIC MANDREL FOR CREATING GRAFT DEVICES

RELATED APPLICATIONS

This application is a National Phase of International Application No. PCT/US2012/069102 filed Dec. 12, 2012, which claims benefit of priority to U.S. Provisional Application No. 61/569,941 filed Dec. 13, 2011, the contents of which are hereby incorporated herein by reference in their entirety.

This application is related to U.S. patent application Ser. No. 13/502,759, filed Apr. 19, 2012; U.S. patent application Ser. No. 13/515,996, filed Jun. 14, 2012; International Patent Application Serial Number PCT/US2012/21209, filed Jan. 13, 2012; and International Patent Application Serial Number PCT/US2012/24251, filed Feb. 8, 2012; the contents of each of these related application are incorporated herein by reference in their entirety.

TECHNICAL FIELD

This application relates generally to systems and methods for creating graft devices for a mammalian patient. In particular, this application provides a mandrel for atraumatic insertion into a tubular conduit such as a saphenous vein graft, and a system for applying a restrictive fiber matrix to the tubular conduit.

BACKGROUND

Coronary artery disease, leading to myocardial infarction and ischemia, is currently a leading cause of morbidity and mortality worldwide. Current treatment alternatives include percutaneous transluminal angioplasty, stenting, and coronary artery bypass grafting (CABG). CABG can be carried out using either arterial or venous conduits and is generally the most effective and most widely used treatment to combat coronary arterial stenosis, with nearly 500,000 procedures being performed annually. In addition, there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 127,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) usually require clinical intervention such as an additional surgery.

IH accounts for 20% to 40% of all AVG failures within the first 5 years after CABG surgery. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

SUMMARY

For these and other reasons, there is a need for devices and methods which provide enhanced AVGs and other grafts for mammalian patients. Desirably the devices will improve long term patency and minimize surgical and device complications.

Developing a reliable means to prevent the early events of the IH process would contribute to improvements in the outcome of arterial bypass procedures. Therefore, provided herein is a method of mechanically conditioning and otherwise treating and/or modifying an arterial vein graft, or other tubular conduit such as living tissue or artificial conduits. To this end, provided herein is a method of applying a restrictive fiber matrix to a tubular conduit to create a graft device. The tubular conduit is placed in a fiber application device such as an electrospinning unit, and a restrictive fiber matrix is applied to surround the tubular conduit. In some particular non-limiting embodiments, the tubular tissue is a vein, such as a saphenous vein, that is used, for instance, in an arterial bypass procedure, such as a coronary artery bypass procedure.

In some aspects, a system for applying a fiber matrix onto a tubular conduit can comprise a tubular conduit, a mandrel and a fiber matrix delivery assembly. The tubular conduit comprises an inner surface and an outer surface. The mandrel comprises an elongate shaft and a rolling membrane. The fiber matrix delivery assembly can be constructed and arranged to receive the mandrel and to apply a fiber matrix to the tubular conduit. The mandrel can be constructed and arranged such that advancement of the elongate shaft causes the rolling membrane to engage with the inner surface of the tubular conduit. Advancement of the elongate shaft may cause the rolling membrane to fold over onto itself, such as to atraumatically engage the inner surface of the tubular conduit. The folding over action of the rolling membrane limits (e.g., minimizes) creation of sliding frictional forces between the rolling membrane and the tubular conduit. The elongate shaft can be expandable, such that expansion of the shaft causes the rolling membrane to engage the inner surface of the tubular conduit.

The mandrel can be constructed and arranged such that retraction of the mandrel causes the rolling membrane to disengage with the tubular conduit inner surface, such as an atraumatic disengagement and/or a disengagement with minimal creation of sliding frictional forces between the rolling membrane and the tubular conduit. The mandrel can include a collar wherein the rolling membrane comprises a first end attached to the elongate shaft and a second end attached to the collar. The mandrel can be relatively straight or curved, and can include a lumen such as a guidewire lumen. In some embodiments, such mandrel elongate shaft includes a preattached guidewire extending from its distal end.

The rolling membrane can be comprised of one or more flexible materials such as a material selected from the group consisting of: polyester; polyamide; polyethylene terephthalate; crosslinked polyethylene; polyurethane; polyvinylchloride; polytetrafluoroethylene; nylon; polyether block amides; silicone; polyether; and combinations of these. The rolling membrane can comprise a first surface and a second surface, such as a first surface configured to transition from an inward orientation to an outward orientation. The first surface can be configured to engage the inner surface of the tubular conduit.

One or more axial stiffeners can be positioned on and/or within the rolling membrane. The one or more axial stiffeners can be configured to roll over onto itself, can have a preferred bending moment, and/or can have an aspect ratio greater than 2:1. The one or more axial stiffeners can be constructed and arranged to reduce one or more motions of the rolling membrane such as a motion selected from the group consisting of: twisting; folding; collapsing; and combinations of these motions. An axial stiffener can comprise a thickened portion of the rolling membrane. An axial stiffener can comprise similar or different materials to the materials of the rolling membrane. In some embodiments, the axial stiffener comprises a material selected from the group consisting of: a metal foil; a superelastic metal sheet; an elastomeric sheet; and combinations of these.

The system can include a pressurization assembly including a pressurization area constructed and arranged to provide axial support to the rolling membrane as the rolling membrane folds over onto itself. A collar can be attached to one end of the rolling membrane, and the collar can be sealed to the elongate shaft, such as via an O-ring. A pressurization port can be in fluid communication with the pressurization area, such as to attach to a syringe or a pump delivering a fluid to the pressurization area. A valve can be included to maintain pressure within the pressurization area and/or to dynamically release pressure when a pressure threshold is reached or exceeded.

The rolling membrane can comprise a single layer or multiple layers. A single layer comprising polymer and metal can be included. A multiple layer rolling membrane can include a metal layer, such as a metal layer deposited using metal evaporation; metal sputtering; metal precipitation, or combinations of these. The rolling membrane can be conductive or include a conductive layer, such as a metal layer or a layer including a conductive material such as an iodine or sodium complex. The metal layer can be configured to be electrically charged, such as to create an electromagnetic field used to attract fibers during an electrospinning process. One or more metals can be included in the rolling membrane such as a metal selected from the group consisting of: stainless steel; elgiloy; tantalum; platinum; gold; tungsten; and combinations of these metals.

The rolling membrane can be porous or include one or more porous portions, such as to deliver fluid from one surface to the other, such as to deliver fluid to the tubular conduit. Porosity can be achieved through the inclusion of sideholes, such as radially and/or longitudinally distributed sideholes. The rolling membrane can include a coating, such as a lubricous coating along at least a portion of its inner and/or outer surface. The fiber matrix delivery assembly can comprise an electrospinning unit, typically including at least one nozzle. Alternative fiber delivery assemblies include but are not limited to: a misting assembly; a dipping assembly; a sprayer; a braiding device; a micropatterning device; an injection device; and combinations of these. The fiber matrix delivery assembly can comprise a rotational drive assembly, such as a drive assembly configured to rotate the mandrel. The rotating drive assembly can be attachable to the mandrel and/or to a support attached to the mandrel.

The tubular conduit can comprise one or more segments of tissue, such as saphenous vein graft tissue. The tubular conduit can comprise numerous forms of living tissue, such as tissue selected from the group consisting of: vein; artery; lymphatic duct; vas deferens; tear duct; intestine; esophagus; ureter; urethra; trachea; bronchi; duct tissue; Eustachian tube; fallopian tube; and combinations of these tissues. Alternatively or additionally, the tubular conduit can comprise artificial material, such as a conduit including a material selected from the group consisting of: polytetrafluoroethylene (PTFE); expanded PTFE (ePTFE); polyester; polyurethane; polyvinylidene fluoride/hexafluoropropylene (PVDF-HFP); silicone; polyethylene; polypropylene; polyester based polymer; polyether based polymer; thermoplastic rubber; and combinations of these materials.

According to another aspect, a mandrel comprises an elongate shaft and a rolling membrane. Advancement of the elongate shaft causes the rolling membrane to fold over onto itself.

According to another aspect, methods for applying a fiber matrix onto a tubular conduit can comprise atraumatically inserting a mandrel into a tubular conduit and applying the fiber matrix to the tubular conduit. The mandrel can comprise an elongate shaft and a rolling membrane.

BRIEF DESCRIPTION OF THE DRAWINGS

The accompanying drawings, which are incorporated in and constitute a part of this specification, illustrate various embodiments of the systems and methods described herein, and together with the description, serve to explain the principles of the systems and methods described herein. In the drawings:

FIGS. 2A-2D illustrate a series of side sectional views of the mandrel of FIGS. 1A-1D being removed from an example graft device comprising a tubular conduit and a fiber matrix covering, consistent with the present inventive concepts.

DETAILED DESCRIPTION OF THE DRAWINGS

Figure 1A:
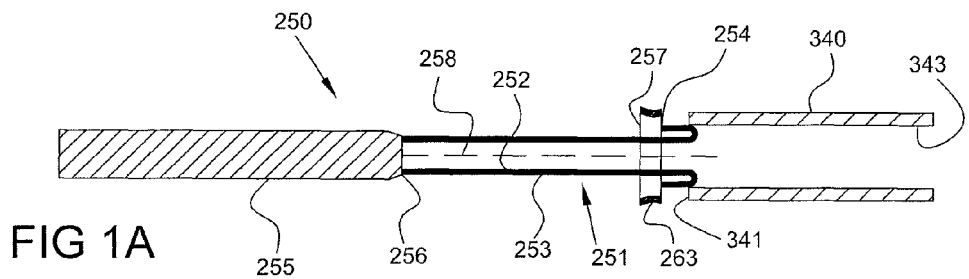
FIGS. 1A-1D illustrate a series of side sectional views of an example mandrel being inserted into a tubular conduit, the mandrel including a rolling membrane consistent with the present inventive concepts.

Reference will now be made in detail to the embodiments of the systems and methods described herein, examples of which are illustrated in the accompanying drawings. The same reference numbers can be used throughout the drawings to refer to the same or like parts.

Provided herein is a system for applying a restrictive fiber matrix to a tubular conduit. The system includes a fiber application unit, such as an electrospinning unit or other piece of equipment constructed and arranged to apply a fiber, such as a polymer fiber, around at least a portion of the outer surface of a tubular conduit, such as a harvested blood vessel. A mandrel is inserted into the tubular conduit, and the fiber application unit operably receives the mandrel with the attached tubular conduit, such that the fiber matrix can subsequently be applied to the tubular conduit. After application of the fiber matrix, the mandrel is removed from the tubular conduit. It is desirable to reduce or eliminate trauma caused to the tubular conduit during insertion and removal of the mandrel. The mandrel can include a rolling membrane configured to minimize such trauma. The rolling mandrel is constructed and arranged to roll over onto itself during insertion such that sliding and/or twisting and resultant sliding and/or twisting forces between the mandrel and the inner lumen of the tubular conduit are reduced (e.g., minimized).

Numerous forms of fiber matrix delivery assembly can be used, including but not limited to: electrospinning assemblies; misting assemblies; dipping assemblies; spray assemblies; braiding assemblies; micropatterning assemblies; injection assemblies; and combinations of these.

The fiber matrix delivery assembly can include a rotational drive mechanism such as a drive including one or more motors, which rotate the assembly of the mandrel and tubular conduit. While rotating, one or more types of fibers, such as polymer fibers, are delivered by a polymer delivery assembly, for example through at least one nozzle that translates back and forth in an oscillating motion along the length of the tubular conduit as fiber is applied. One or more nozzles can be included, and each nozzle can deliver a single fiber, or multiple fibers, simultaneously. Alternatively or additionally, the one or more nozzles can be rotated and/or translated about the mandrel and tubular conduit, reducing or avoiding the need for mandrel rotation.

The graft device produced by the systems, methods and devices discussed herein typically include a tubular conduit and a surrounding fiber matrix covering. The tubular conduit can comprise a hollow tube conduit used as a means for fluid to flow between a first body space and a second body space. The tubular conduit can comprise tissue, such as autologous, allogeneic, or xenogeneic tissue, including, without limitation: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). The tubular conduit can also be a tissue engineered vascular or other tissue graft, comprised of a covering material (biological or synthetic-based) that is seeded with adult differentiated cells and/or undifferentiated stem cells, or unseeded. The covering can be treated with synthetic, biological, or biomimetic cues, such as to improve anti-thrombogenicity or other tissue-specific functionalities, or to enhance selective or non-selective cell repopulation once implanted in vivo. The covering can be treated with one or more chemotactic or chemoattractant agents and can include selective degradation sites. Alternatively or additionally, the tubular conduit can include an artificial, non-tissue structure, such as polytetrafluoroethylene (PTFE); expanded PTFE (ePTFE); polyester; polyvinylidene fluoride/hexafluoropropylene (PVDF-HFP); silicone; polyethylene; polypropylene; polyurethane; polyester based polymer; polyether based polymer; thermoplastic rubber; and combinations of these. The graft device can have a relatively uniform cross section, or a cross section that varies (e.g. in diameter or cross sectional geometry) along the length of the tubular conduit. The graft device can be straight or curved. Additional graft devices, systems and methods are also described in applicant's co-pending U.S. patent application Ser. No. 13/515,996, filed Jun. 14, 2012 and entitled "GRAFT DEVICES AND METHODS FOR USE"; International Patent Application Serial Number PCT/US2012/21209, filed Jan. 13, 2012 and entitled "APPARATUS FOR CREATING GRAFT DEVICES"; and International Patent Application Serial Number PCT/US2012/24251, filed Feb. 8, 2012 and entitled "SYSTEM AND MANDREL FOR CREATING GRAFT DEVICES"; each of which is incorporated herein by reference in their entirety.

In some embodiments, the graft device includes a restrictive matrix including polymers such as bioerodible polymers and/or non-bioerodible polymers. The fiber matrix can comprise a thermoplastic co-polymer made of two or more materials, such as a first material and a harder second material. In some embodiments, the co-polymer has a durometer of approximately 55D, with approximately an even amount of the softer material and the harder material. The softer material can include polydimethylsiloxane (PDMS) and a polyether-based polyurethane. The harder material can include aromatic methylene diphenyl isocyanate (MDI).

The applied fiber can comprise a polymer or polymer blend fiber that is applied when the one or more polymers are mixed with one or more solvents. Alternatively or additionally, polymers can be applied in liquid form achieved through other means such as by elevated temperature or by the use of monomers which are activated and polymerized during or shortly after processing. Examples of polymers include natural polymers, synthetic polymers, and blends of natural and synthetic polymers. For example and without limitation, natural polymers include: silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers.

As used herein, the descriptor "tubular conduit" does not refer specifically to a geometrically perfect tube having a constant diameter and a circular cross-section. It also embraces tissue and artificial conduits having non-circular and varying cross sections, and can have a variable diameter, and thus any shape having a contiguous wall surrounding a lumen (that is, they are hollow), and two openings into the lumen such that a liquid, solid, or gas can travel from one opening to the other. The openings can be at the end of the conduit, or at any location along the length of the conduit. The tubular conduit can be created from a membranous material, such as a membrane that comprises a sheet that is joined along a seam to create a substantially cylindrical form. The tubular conduit can comprise harvested tissue that is formed or reformed into a tube or other structure.

The covering can be substantially or essentially contiguous about an internal or external wall of a tubular conduit, meaning that the covering forms a continuous, supportive ring on a surface and about a circumference of a portion, but not necessarily over the entire surface (e.g., length) of the tubular conduit. The covering can be "restrictive", meaning that the covering is in substantial contact with the outer surface of the tubular conduit such as to provide an incremental physical property in addition to the underlying property of the tubular conduit. Alternatively, the covering can be narrowly spaced and proximate to the outer surface of the tubular conduit (e.g. to restrict after an initial unrestricted expansion). The covering can also be "constrictive", meaning that the diameter of the tubular conduit is reduced by the application of the covering. Restrictive coverings can be used to reinforce, restrict, hinder and/or prevent substantial circumferential and/or longitudinal expansions of the tubular conduit, such as when the graft device is a tubular conduit used as a bypass graft and is exposed to arterial pressure; or otherwise when the tubular conduit is radially and/or longitudinally expanded. The degree of restriction by the covering typically is such that when exposed to internal pressure, such as typical arterial pressures, the tubular conduit is limited (e.g., prevented) from distending to the extent that would occur without such restriction. Constrictive coverings can be used to match the internal diameter of the tubular conduit to the internal diameter of the target tissue being connected by the tubular conduit. For example, quite often a vein being used as a coronary artery bypass graft has a considerably larger internal diameter than the target coronary artery being bypassed. In order to reduce flow disturbances, it is advantageous to match the internal diameter of the graft (conduit) to the internal diameter of the bypassed coronary artery. The covering can be durable or temporary, such as when the restrictive nature of a biodegradable covering can decline over time. The covering can have a relatively uniform cross section, or a cross section that varies along the length of the covering.

The covering can be applied to a tubular conduit that has either a cylindrical or non-cylindrical (e.g. oval) mandrel inserted in its lumen. Mandrels are typically constructed and arranged to be removed from the graft device without damaging the tubular conduit or any other portion of the graft device. The mandrel can comprise an expandable tube, such as a furled tube or other radially or longitudinally expandable structure, such that the mandrel can be unfurled or otherwise radially or longitudinally constricted for atraumatic removal from the tubular conduit of the graft device. The mandrel can transform from a rigid state to a flexible state, and vice versa. Mandrels can have relatively constant cross-sectional geometries, or cross-sections that vary, such as mandrels including a first portion with a circular cross sections and a second portion with an oval cross sections, and tapered mandrels.

The mandrel can be relatively straight, or it can have a non-linear geometry. In some embodiments, a mandrel comprises a three dimensional geometry intended to match anatomical locations of a patient, such as an anatomical topography proximate two or more intended anastomotic connections for the graft device. Mandrels can include both straight and curved portions. The mandrel can be a malleable or otherwise deformable structure which is shaped during a surgical procedure. Alternatively, the mandrel can be fabricated based upon one or more patient images created during an imaging procedure, such as an imaging procedure selected from the group consisting of: X-ray such as still image X-ray or fluoroscopy; MRI (including Functional MRI), CT scan, PET Scan, SPECT, Scintigraphy, NMR, Ultrasound, PCT scan, Optical Coherence Tomography (OCT), CCD camera; film camera; and combinations of these.

In coverings applied to a tubular conduit with an electrospinning process, an electrically conductive mandrel, for example, a rod that is formed of a conductive material such as stainless steel, can be placed inside a tubular conduit, such as a vein, and polymer fibers deposited about the circumference of at least a portion of the tissue by rotation or other movement of the mandrel, movement of the nozzles supplying the fiber, and/or movement of the electrical field directing the fibers toward the mandrel. Thickness, as well as other mechanical and physical properties of the covering, can be controlled by adjusting the chemical or physical properties of the polymer solution to be deposited (e.g. adjusting the conductivity, surface tension and/or viscosity of the solution); varying the infusion rate of the polymer solution; modifying the electric field between the polymer source and the mandrel or target; adjusting duration of the electrospinning; and combinations of these. Use of a more or less viscous polymer compositions can result in thicker or thinner fibers, respectively, affecting the mechanical properties (e.g. the elastic, viscoelastic, and plastic properties), the level of polymer crystallinity, the solvent content (the amount and feature of nodal points obtained by solvent bonding also affects the mechanical and physical properties of the material), and the porosity of the deposited polymer. The thickness of the covering and fibers within the covering can be selected to determine numerous device properties, such properties including but not limited to: stiffness and buckling stability; mechanical stability under sustained levels of stress of cyclic deformations; speed of biodegradation of the covering; permeability of the material; and combinations of these. Biodegradation can also be varied by altering the surface finish, wettability, porosity or other characteristic of the fibers, as well as by introducing functional domains to the fiber matrix structure (e.g., cleavage domains activated in response to natural or artificial cues). These parameters can be altered by using solvents or diluents that evaporate at varying rates and/or by adding purifiers to the solution, such as immiscible fluids, emulsified particles or undissolved solids that can be later dissolved such as to create pores. Alternatively or additionally, other modifying agents can be added to the polymer prior to electrospinning such as detergents or surfactants. These polymer solution parameters are optimized, depending on the end-use of the covering, to achieve a desired or optimal physiological effect. Functional domains can be added by covalent bonding to the fiber matrix structure. Thickness and other features (e.g. fiber size, porosity, nodal points, molecular alignment; fiber crystallinity or mechanical properties) can be varied along the length of a target in a regular or irregular fashion, such as in creating a target that is thicker at one or both ends, in the center, or as with a location-dependent symmetrical or asymmetrical thickness. In some embodiments, the thickness is varied by moving an electrospinning nozzle back and forth slowly near a specific circumferential location, thereby depositing more material proximate to that area or to create recurring features. In some embodiments, covering thickness is determined by the thickness of the tubular conduit, such as when the covering is thicker at a circumferential portion of the tubular conduit that is thinner than other circumferential portions of the tubular conduit. In some embodiments, thickness and/or other properties are varied by applying a field modification proximate to the polymer source or target to alter the trajectory of the fibers. Such a field modification can be produced, for example, by a metal plate that is inserted into the area adjacent to the source or target that is at a sufficiently different voltage potential than the source such that the resulting field alters the trajectory of the fibers.

Electrospinning can be performed using two or more nozzles, wherein each nozzle can be a source of a different polymer solution. The nozzles can be biased with different biases or the same bias in order to tailor the physical and chemical properties of the resulting non-woven polymeric mesh. Additionally, multiple different targets (e.g. mandrels) can be used. When the electrospinning is to be performed using a polymer suspension, the concentration of the polymeric component in the suspension can also be varied to modify the physical properties of the matrix. For example, when the polymeric component is present at relatively low concentration, the resulting fibers of the electrospun matrix have a smaller diameter than when the polymeric component is present at relatively high concentration. Without any intention to be limited by this theory, it is believed that lower polymer concentration solutions have a lower viscosity, leading to greater extrusion or attenuation of the fibers to produce thinner fibers. One skilled in the art can adjust polymer solution chemical and physical properties and process parameters to obtain fibers of desired characteristics, including fibers whose characteristics change along the length or width of the target.

Coverings can be constructed and arranged in a manner specific to a patient morphological or functional parameter. These parameters can be selected from the group consisting of: vessel size such as inside diameter, outside diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; existing varicosities and other vascular pathologies; vessel electrical impedance; specific patient genetic factors or traits; specific patient pathologies; and combinations of these.

Coverings of arterial vein grafts can be processed in a way to achieve a certain blood flow rate or shear stress within the treated arterial vein graft. In some configurations, shear stress within the arterial vein graft is between 2 dynes/cm$^2$ to 30 dynes/cm$^2$, and in some cases, 12 dynes/cm$^2$ to 20 dynes/cm$^2$ is achieved. Coverings can be processed in a way to control the oxygen, nutrients, or cellular permeabilities between the extravascular tissues and the abluminal surface of the treated hollow tissue. Such permeabilities depend on the covering chemical and physical properties, the pore size distribution, porosity, and pore interconnectivity. Generally, oxygen, nutrients, and cellular (e.g., angiogenesis related cells, pericytes, endothelial cells, endothelial progenitor cells, inflammation-related cells; macrophages, etc.) permeability are required to improve the treated hollow tissue in vivo remodeling and healing process. To this end, the pore size range can be between 1 microns and 1000 microns, for example between 100 microns and 250 microns, and the porosity range can be between 50% and 95%, for example between 60% and 90%. Pore size and other porosity parameters can be achieved through one or more post-processing steps performed after electrospinning or other fiber application process. Porosity can be adjusted with a mechanical tool such as a microneedle punch assembly, with energy such as with a laser and/or chemically such as with an etching or other material removal process. In some embodiments, the pores are highly interconnected so that a relatively straight path along the radial direction of the fiber matrix can be traced from most of the pores across the total thickness of the matrix. Polymers used can be hydrophobic.

Radial restriction and constriction of saphenous vein grafts has been achieved with stent devices placed over the vein prior to anastomosing the graft to the targeted vessels. The devices described herein can provide numerous advantages over the stent approaches. The devices described herein can have one or more parameters easily customized to a parameter of the harvested vessel and/or another patient parameter. The covering can be customized to a harvested vessel parameter such as geometry, such as to reduce the vein internal diameter to produce desired flow characteristics. The covering can be customized to other harvested vessel parameters such as the number and location of side branches or other vessel irregularities, such as to produce an internal lumen with a consistent size along the length of the graft despite the presence of external topographical irregularities of the harvested vessel including but not limited to: side branches with ligations and metal vascular clips, valves, adventitial residues, as well as the natural taper (uniform or non-uniform). The covering can be customized to a target vessel parameter (e.g., the aorta and diseased artery), such as to be compatible with vessel sizes, mechanical properties, and/or locations. The covering can be modified to simplify or otherwise improve the anastomotic connections, such as to be reinforced in the portion of the device that is anastomosed (e.g., portion where suture and/or clips pass through) and/or to protrude beyond the length of the tubular conduit and overlap other members connected to the graft device.

The devices described herein can be made to a wide array of lengths during the procedure, without the need for cutting, such as the cutting of a stent device, which might create dangerously sharp edges. The covering is applied to the tubular conduit in an automated, controlled, repeatable manner, by an apparatus such as an electrospinning instrument. The ends of the covering are atraumatic, avoiding tissue damage or irritation at the anastomotic sites. In addition, the coverings can be constructed and arranged to be easily and atraumatically removable from the tubular conduit, such as to apply another covering. Stent devices are applied manually by a clinician, require significant manipulation which could cause iatrogenic damage, have issues with reproducibility and accuracy limitations, and are difficult to reposition or remove, particularly without damaging the harvested vessel. In some embodiments where the tubular conduit comprises a vessel, the conformal covering disclosed herein follows the natural external geometry of the vessel (e.g., adventitial tissue accumulations, ligated branches, etc.) without resulting in a net inward compression caused by external application of a constant tubular structure onto a naturally variable tubular tissue.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, the term "polymer composition" is a composition comprising one or more polymers. As a class, "polymers" includes homopolymers, heteropolymers, co-polymers, block polymers, block co-polymers, alloys or blends and can be both natural and synthetic. Homopolymers contain one type of building block, or monomer, whereas co-polymers contain more than one type of monomer. For example and without limitation, polymers comprising monomers derived from alpha-hydroxy acids including polylactide, poly (lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

The polymer or polymers typically can be selected so that it degrades (e.g. it is bioabsorbed, has decreased mechanical strength, and/or otherwise changes one or more mechanical properties) in situ over a time period to optimize mechanical conditioning of the tissue or other tubular conduit. Non-limiting examples of useful in situ degradation rates include between 2 weeks and 1 year, and increments of 1, 2, 4, 8, 12, and, 24 weeks therebetween. Biodegradation can occur at different rates along different circumferential and/or longitudinal portions of the covering. A biodegradation rate of the polymer covering can be manipulated, optimized or otherwise adjusted so that the covering degrades over a useful time period. For instance, in the case of a coronary artery bypass, it is desirable that the covering dissolves over 2 weeks or, more typically, 10 weeks or more, so as to prevent substantial sudden circumferential wall stress on the graft. The polymer degrades over a desired period of time so that the mechanical support offered by the polymer covering is gradually reduced over that period and the vein would be exposed to gradually increasing levels of circumferential wall stress (CWS).

The biodegradable polymers useful herein also can be elastomeric. Generally, any elastomeric polymer that has properties similar to that of the soft tissue to be replaced or repaired is appropriate. For example, in certain embodiments, the polymers used to make the wrap are highly distensible. Non-limiting examples of suitable polymers include those that have plastic yield strain of 10% to 100% and breaking strain of from 100% to 1700%, more preferably plastic yield strain between 15% and 100%, and breaking strain between 200% and 800%, and even more preferably plastic yield strain between 50% and 100%, and breaking strain between 200% and 400%. Further, it is often useful to select polymers with ultimate tensile stress between 10 kPa and 30 MPa, more preferably between 5 MPa and 25 MPa, and even more preferably between 8 MPa and 20 MPa. In some embodiments, polymeric fiber matrices with plastic yield tensions between 1 N/cm and 10 N/cm, preferably between 2 N/cm and 5 N/cm are used. In certain embodiments, the elastic modulus calculated for physiologic levels of strain is between 10 kPa to 100 MPa, more preferably between 0.5 MPa and 1.5 MPa, and even more preferably between 0.5 MPa and 1.0 MPa.

As used herein, a "fiber" comprises an elongated, slender, thread-like and/or filamentous structure with or without branching fibers. Fibers can be solid (including composite materials such as concentric or particulate-included composite materials) or hollow, and the fibers can have a smooth, rough, or porous surface.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

Referring now to FIGS. 1A-1D, a series of steps for inserting a mandrel into a tubular conduit are illustrated, consistent with the present inventive concepts. Mandrel 250 includes a rolling membrane 251, constructed and arranged to minimize trauma to tubular conduit 340 during insertion of mandrel 250 into tubular conduit 340. Tubular conduit 340 can comprise one or more segments of living and/or artificial tissue, as has been described hereabove. FIGS. 1A-1D are sectional views, while hatching is removed from FIGS. 1B-1D for illustrative clarity. Mandrel 250 comprises shaft 255 with distal end 256. Distal end 256 can include the taper shown, such as to limit or reduce (e.g., prevent) trauma as shaft 255 is advanced into and through conduit 340. Shaft 255 can be a solid or hollow shaft, and shaft 255 can include one or more lumens, not shown but typically configured as a guidewire lumen as is shown in FIGS. 7A-7C herebelow. Shaft 255 can be rigid, flexible, or include both rigid and flexible portions. Shaft 255 can be configured to transition to a rigid state, such as the expanding shaft of FIGS. 6A-B described herebelow. Shaft 255 can comprise a length between 3 cm and 30 cm, and can be sized to one or more tubular segments, such as one or more harvested segments of a saphenous vein.

Attached to distal end 256 is a tubular, rolling membrane 251. Membrane 251 can be attached to distal end 256 in one or more ways, such as with an adhesive or a weld such as an ultrasonically formed weld. Alternatively, membrane 251 can be removably attached to distal end 256, such as an attachment with an elastomeric band, not shown but configured to provide sufficient retention force to limit (e.g., prevent) movement between membrane 251 and shaft 255 during insertion of mandrel 250 into a vein graft or other tubular conduit.

Membrane 251 comprises a first surface 252, a second surface 253, an end 254, and a central axis 258. End 254 has been folded over onto itself and attached to collar 257 as shown. Collar 257 typically comprises a rigid or semi-rigid material, such as a collar made from one or more metals or hard plastics. Mandrel 250 is configured such that advancement of shaft 255 to the right of the page as shown in FIGS. 1A-1D, while maintaining the position of collar 257, causes membrane 251 to roll over onto itself with sequential segments of first surface 252 transitioning from being oriented inward (i.e. toward central axis 258) to being oriented outward (i.e. away from central axis 258), while corresponding sequential segments of second surface 253 transition from being oriented outward to being oriented inward. Mandrel 250 can include means of axially distending membrane 251, such as to aid in insertion and/or removal of membrane 251 into and/or from tubular conduit 340, not shown but such as is described in reference to FIGS. 7A-7C herebelow.

Membrane 251 can comprise one or more materials configured to be flexible and allow membrane 251 to fold over onto itself, such as when in a tubular geometry. In some embodiments, membrane 251 comprises a material selected from the group consisting of: polyester, polyamide, polyethylene terephalate, crosslinked polyethylene, polyurethane, polyvinylchloride, polytetrafluoroethylene, nylon, polyether block amides, silicone, POC, polyether, and any combinations of these. Membrane 251 can comprise one or more coatings, such as a lubricious coating.

Figure 1B:
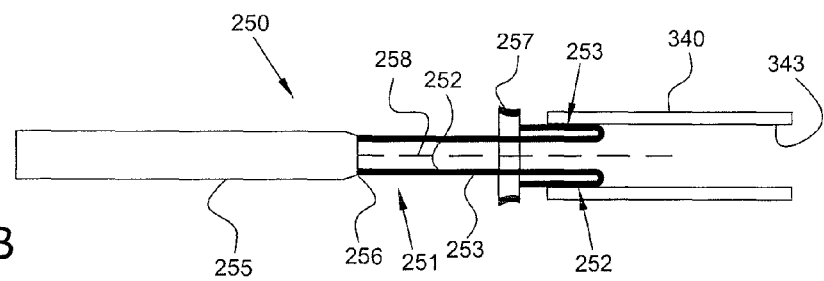

Referring specifically to FIG. 1A, the distal end 256 of mandrel 250 is positioned proximate tubular conduit 340, such that an initial segment of first surface 252 facing outward is proximate end 341 of conduit 340. In FIG. 1B, shaft 255 is partially advanced (to the right of the page as shown), while collar 257 is held in place, such as by the hands of an operator or a tool being controlled by an operator, hands or tools not shown. Collar 257 can include a recess to improve gripping of collar 257 by an operator's hand or gripping tool, such as recess 263. Additional segments of first surface 252 have folded over while atraumatically engaging inner surface 343 of conduit 340. This engagement comprises a rolling engagement of first surface 252 with inner surface 343, avoiding creation of sliding, twisting and/or other frictional forces that may cause trauma to conduit 340.

Figure 1C:
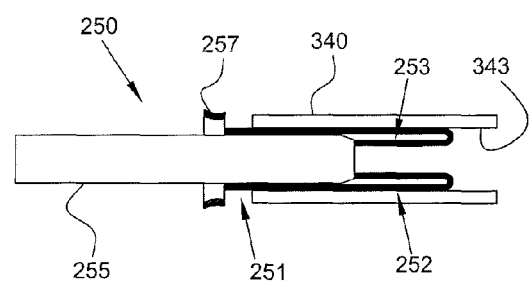

In FIG. 1C, shaft 255 has been further advanced, while collar 257 has been maintained in place as described above. Additional segments of first surface 252 have folded over while rollingly engaging additional segments of inner surface 343 of conduit 340. A distal portion of shaft 255 has entered the lumen of conduit 340, while avoiding direct contact with inner surface 343.

Figure 1D:
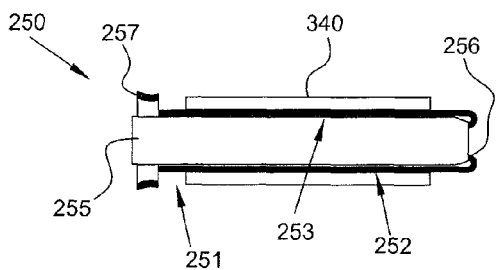

In FIG. 1D, shaft 255 has been fully advanced, while collar 257 has been maintained in place as described above. The majority of length of first surface 252 has folded over while rollingly engaging the full length of inner surface 343 of conduit 340. Shaft 255 is positioned within the lumen of conduit 340 as shown. Mandrel 250 and tubular conduit 340 are ready for insertion into a fiber matrix delivery assembly, such as the electrospinning unit described in reference to FIG. 8 herebelow.

Figure 1E:
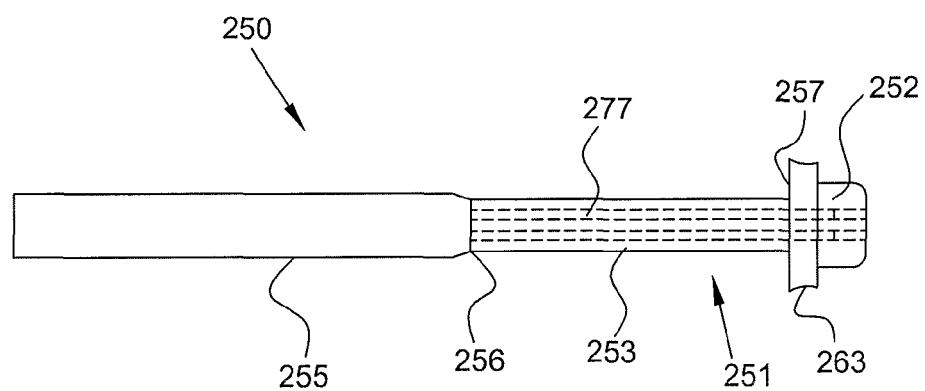
FIG. 1E illustrates a side view of an example mandrel including multiple axial stiffeners, consistent with the present inventive concepts.

Referring now to FIG. 1E, a side view of a mandrel comprising a membrane including multiple axial stiffeners is illustrated, consistent with the present inventive concepts. Mandrel 250 includes similar components and functionality as mandrel 250 of FIGS. 1A-1D hereabove. One or more axial stiffeners 277 are positioned within the wall of membrane 251. Alternatively or additionally, axial stiffeners 277 can be positioned on first surface 252 and/or second surface 253, such as via an adhesive attachment. Axial stiffeners 277 can comprise elongate flexible sheets oriented along the major axis of membrane 251. Stiffeners 277 are configured to roll over onto themselves when attached to membrane 251, while providing column strength to and preventing undesired distortions of membrane 251, such as undesired twisting, folding, collapsing or other undesired movement of membrane 251. Stiffeners 277 can comprise a preferred bending moment, such as the preferred bending moment provided in a rectangular cross section with an aspect ratio greater than 2:1, preferably greater than 3:1 and more preferably greater than 4:1. Axial stiffeners 277 can comprise a thickened portion of membrane 251, such as a stiffener of the same material and/or made in the same process as used to create membrane 251. Alternatively or additionally, axial stiffener 277 can comprise a different material such as a material selected from the group consisting of: a metal foil; a superelastic metal sheet; an elastomeric sheet; and combinations of these.

Referring now to FIGS. 2A-2D, a series of steps for removing the mandrel of FIGS. 1A-1D from a graft device are illustrated, consistent with the present inventive concepts. The graft device comprises the tubular conduit with a fiber matrix covering. FIGS. 2A-2D are sectional views, while hatching has been removed from FIGS. 2A-2C for illustrative clarity.

Referring specifically to FIG. 2A, the tubular conduit 340 and mandrel 250 have been removed from a fiber matrix delivery assembly. A fiber matrix 320 was applied to tubular conduit 340 to create a graft device 300, such as in with a system and method described in reference to FIG. 8 herebelow. First surface 252 of membrane 251 is oriented outward and in contact with inner surface 343 of conduit 340, while second surface 253 is oriented inward and in contact with shaft 255.

In FIG. 2B, shaft 255 has been partially retracted (to the left of the page as shown), while maintaining collar 257, as has been described in reference to FIGS. 1A-1D hereabove. Segments of first surface 252 have folded over while atraumatically disengaging inner surface 343 of conduit 340. This disengagement comprises a rolling disengagement of first surface 252 with inner surface 343, avoiding creation of sliding, twisting and/or other frictional forces that may cause trauma to conduit 340.

In FIG. 2C, shaft 255 has been further retracted, while collar 257 has been maintained in place, as described above. Additional segments of first surface 252 have folded over while rollingly disengaging additional segments of inner surface 343 of conduit 340. Shaft 255 no longer resides within the lumen of conduit 340.

In FIG. 2D, shaft 255 has been fully retracted, while collar 257 has been maintained in place, as described above. Mandrel 250 has been fully removed from graft device 300 such that graft device 300 can be implanted in a patient, such as in a cardiac or other bypass procedure.

Figure 3A:
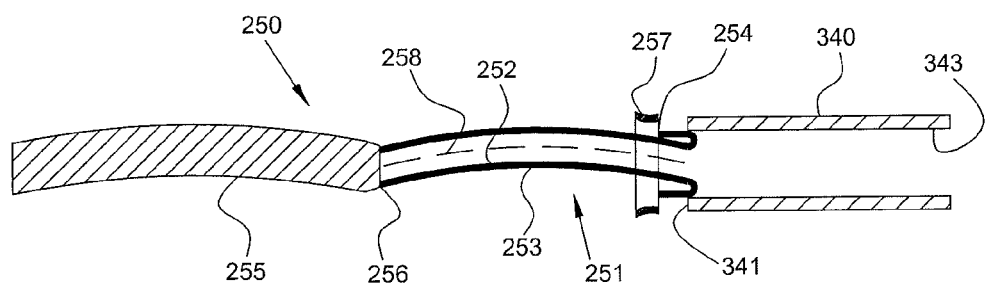
FIG. 3A illustrates a side sectional view of an example curved mandrel including a rolling membrane, prior to insertion into a tubular conduit, consistent with the present inventive concepts.

Referring now to FIG. 3A, a side sectional view of a curved mandrel including a rolling membrane, prior to insertion into a tubular conduit, is illustrated, consistent with the present inventive concepts. Mandrel 250 includes a rolling membrane 251, constructed and arranged to minimize trauma to tubular conduit 340 during insertion of mandrel 250 into tubular conduit 340. Tubular conduit 340 can comprise one or more segments of living and/or artificial tissue, as has been described hereabove. Mandrel 250 is shown positioned proximate end 341 of tubular conduit 340, ready to be inserted into conduit 340. Mandrel 250 comprises shaft 255 with distal end 256, such as a tapered distal end. Shaft 255 can be a solid or hollow shaft, and it can include one or more lumens, not shown. Shaft 255 can be rigid, flexible, or include both rigid and flexible portions. Attached to distal end 256 is a tubular membrane 251. Membrane 251 comprises a first surface 252, a second surface 253, and an end 254. End 254 has been folded over onto itself and attached to collar 257 as shown. Mandrel 250 is configured such that advancement of shaft 255 to the right of the page as shown in FIG. 3A, while maintaining the position of collar 257, causes membrane 251 to roll over onto itself with sequential segments of first surface 252 transitioning from being oriented inward (i.e. toward central axis 258) to being oriented outward (i.e. away from central axis 258), while corresponding sequential segments of second surface 253 transition from being oriented outward to being oriented inward.

Figure 3B:
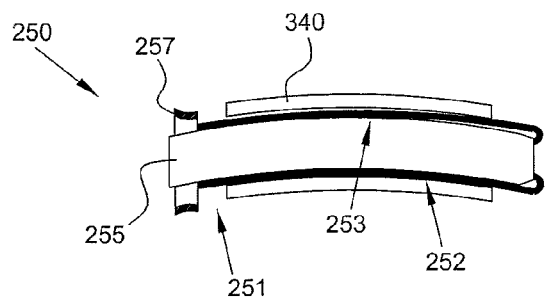
FIG. 3B illustrates a side sectional view of the curved mandrel of FIG. 3A after insertion into the tubular conduit, consistent with the present inventive concepts.

FIG. 3B illustrates a side sectional view of the curved mandrel 250 of FIG. 3A after insertion into tubular conduit 340, such as is in an insertion method described in reference to FIGS. 1A-1D hereabove. Hatching has been removed from FIG. 3B for illustrative clarity.

Shaft 255 and/or membrane 251 can comprise a curved orientation, as is shown in FIGS. 3A-3B. In a typical embodiment, at least shaft 255 can have a curved orientation such that when mandrel 250 and tubular conduit 340 are inserted in a fiber matrix delivery system, such as the system described in reference to FIG. 8 herebelow, a non-linear graft device is created, such as a graft device with one or more curved portions configured to ease implantation and/or improve blood flow dynamics after implantation.

While the embodiments shown in FIGS. 3A and 3B include both a shaft and a rolling membrane with a curved geometry, one can be curved while the other is relatively straight. In some embodiments, shaft 255 is curved while membrane 251 is relatively straight and comprises sufficient flexibility to assume the curved shape of shaft 255 when rolled over onto shaft 255. While the embodiments shown in FIGS. 3A and 3B comprise a curved shape with a single radius of curvature, shaft 255 and/or membrane 251 can comprise multiple radii of curvature such as multiple curves that lie in one or more planes.

Figure 4:
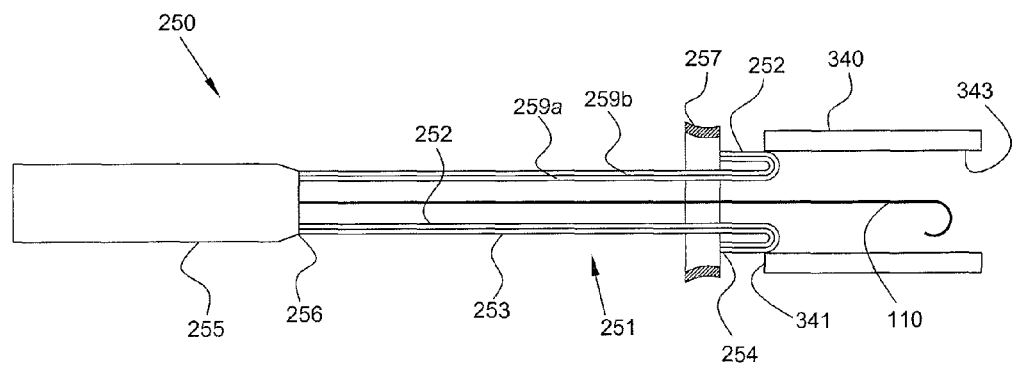
FIG. 4 illustrates a side sectional view of an example mandrel including a multiple layer rolling membrane, prior to insertion into a tubular conduit, consistent with the present inventive concepts.

Referring now to FIG. 4, a side sectional view of a curved mandrel including a multiple layer rolling membrane, prior to insertion into a tubular conduit, is illustrated, consistent with the present inventive concepts. Hatching has been removed from FIG. 4 for illustrative clarity. Mandrel 250 includes a rolling membrane 251, constructed and arranged to minimize trauma to tubular conduit 340 during insertion of mandrel 250 into tubular conduit 340. Tubular conduit 340 can comprise one or more segments of living and/or artificial tissue, as has been described hereabove. Mandrel 250 is shown positioned proximate end 341 of tubular conduit 340, ready to be inserted into conduit 340. Mandrel 250 is constructed and arranged similar to the mandrel of FIGS. 1A-1D, including a similar shaft 255 and collar 257. Shaft 255 of FIG. 4 further includes an attached J-tipped guidewire 110 extending from its distal end 256. Guidewire 110 has been inserted into the lumen of tubular conduit 340. Guidewire 110 typically has the construction of a standard interventional guidewire and includes a soft, flexible tip configured for atraumatic insertion and advancement through the lumen of a blood vessel. Guidewire 110 can include one or more coatings such as a lubricous coating, including but not limited to, a lubricous polymer coating. Alternatively, shaft 255 can include a guidewire lumen, not shown but described in reference to FIGS. 7A-7C herebelow.

Membrane 251 of FIG. 4 comprises a multiple layer tubular construction. Membrane 251 includes inner layer 259a and outer layer 259b. Inner layer 259a has an inner surface, first surface 252. Outer layer 259b has an outer surface, second surface 253. Membrane 251 is attached to distal end 256 of shaft 255 as shown. Distal end 254 of membrane 251 has been folded over onto itself and attached to collar 257. Mandrel 250 is configured such that advancement of shaft 255 to the right of the page as shown in FIG. 4, while maintaining the position of collar 257, causes membrane 251 to roll over onto itself with sequential segments of first surface 252 transitioning from being oriented inward (i.e. toward its central axis) to being oriented outward (i.e. away from its central axis), so as to contact inner surface 343 of conduit 340, while corresponding sequential segments of second surface 253 transition from being oriented outward to being oriented inward.

In some embodiments, membrane layer 259a and 259b comprise different materials. Membrane layer 259a can be configured to deliver one or more agents to conduit 340, via first surface 252. Membrane layer 259a and/or membrane layer 259b can comprise a metal layer such as a metal foil layer or other flexible metal layer. The metal layer can be configured to receive a charge, such as a charge used to electrospin a fiber matrix onto conduit 340, as described in reference to FIG. 8 herebelow. The metal layer can be configured to be evaporated, sputtered or precipitated onto the opposite layer. Alternatively, metal could be blended with a polymer in a single layer membrane construction. Applicable metals include but are not limited to: stainless steel, elgiloy, tantalum, platinum, gold and/or tungsten. Alternatively, a polymer can be compounded with iodine or sodium complex to create one or more layers of membrane that are conductive.

Figure 5:
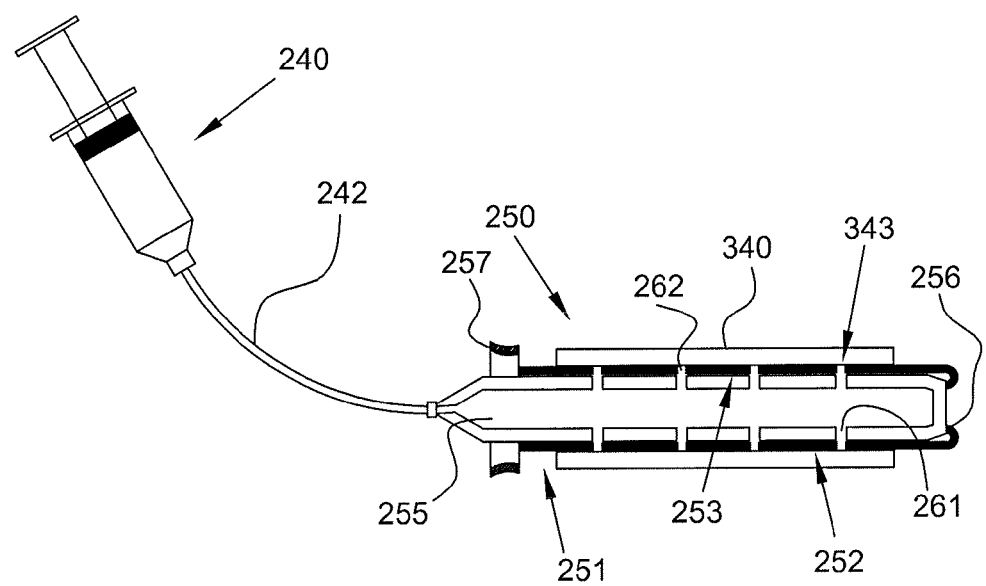
FIG. 5 illustrates a side sectional view of an example mandrel including a permeable rolling membrane after insertion into a tubular conduit, consistent with the present inventive concepts.

Referring now to FIG. 5, a side sectional view of a tubular conduit with a pre-inserted mandrel is illustrated, consistent with the present inventive concepts. The mandrel includes a rolling membrane and is configured for delivery of fluids. Hatching has been removed from FIG. 5 for illustrative clarity. Mandrel 250 includes a rolling membrane 251, constructed and arranged to minimize trauma to tubular conduit 340 during insertion of mandrel 250 into tubular conduit 340. Tubular conduit 340 can comprise one or more segments of living and/or artificial tissue, as has been described hereabove. Mandrel 250 is shown positioned within tubular conduit 340, such as after an insertion method as is described in reference to FIGS. 1A-1D hereabove. Mandrel 250 is constructed and arranged similar to the mandrel of FIGS. 1A-1D, including a similar collar 257. In some embodiments, as depicted in FIG. 5, membrane 251 and shaft 255 can be configured to allow an agent such as a fluid agent to be delivered to the inner wall 343 of conduit 340, such as via the syringe 240 and tubing 242. Numerous fluids can be delivered, such as one or more liquids or gases.

Shaft 255 includes one or more openings, holes 261, and membrane 251 includes one or more openings, holes 262. Shaft 255 comprises a hollow shaft which fluidly attaches to tubing 242. Holes 261 and 262 are positioned such that when mandrel 250 is fully inserted into conduit 340 with first surface 252 folded over (as shown), holes 261 and 262 are sufficiently aligned to allow fluid to pass through holes 261, through holes 262 and into conduit 340 via inner surface 343. Holes 261 and/or 262 can be distributed radially and/or longitudinally. In some embodiments, holes 261 and 262 are of similar diameter or cross-sectional area. In other embodiments, holes 261 and 262 are of dissimilar diameter or cross-sectional area. In yet other embodiments, shaft 255 and/or membrane 251 comprise a material with sufficient permeability or porosity to allow one or more agents to pass therethrough, without a specific need for holes. Delivered agents can be configured to perform one or more functions such as a function selected from the group consisting of: hydrate the tubular conduit; deliver one or more drugs, cells or other agents to the tubular conduit; modify the tubular conduit; cool or warm the tubular conduit; and combinations of these. Typical agents delivered include but are not limited to: anti-infective agents; anti-thrombotic agents; hydrating agents; cooling agents; warming agents; vasodilating agents; cells; and combinations of these.

Figure 8:
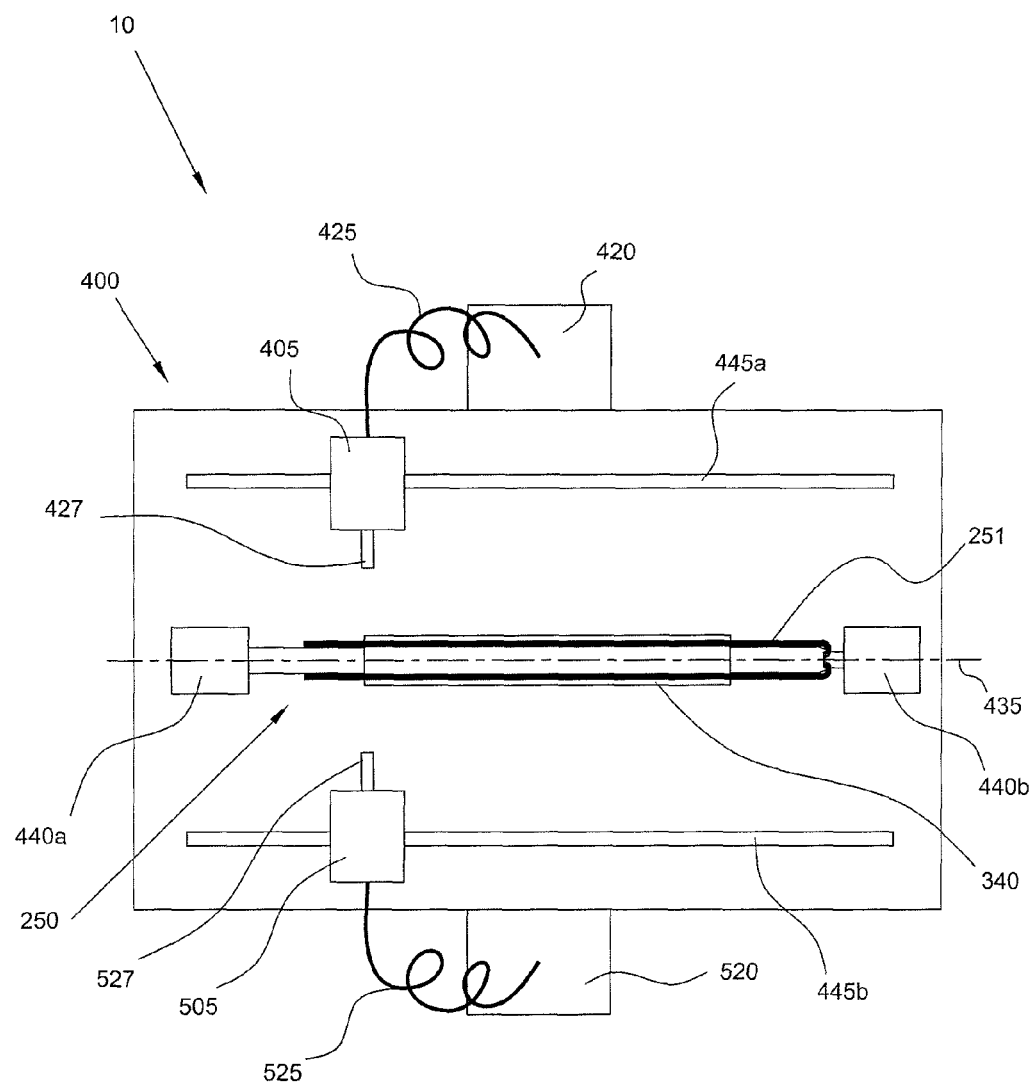
FIG. 8 illustrates a side view of an example system including an example fiber matrix delivery assembly, a tubular conduit, and a mandrel including a rolling membrane, consistent with the present inventive concepts.

Agents can be applied prior to, during and/or after application of a fiber matrix, such as a fiber matrix applied using the system described in reference to FIG. 8 herebelow. After fiber matrix application, mandrel 250 can be removed, such as by using the removal method described in reference to FIGS. 2A-2D hereabove.

Figure 6A:
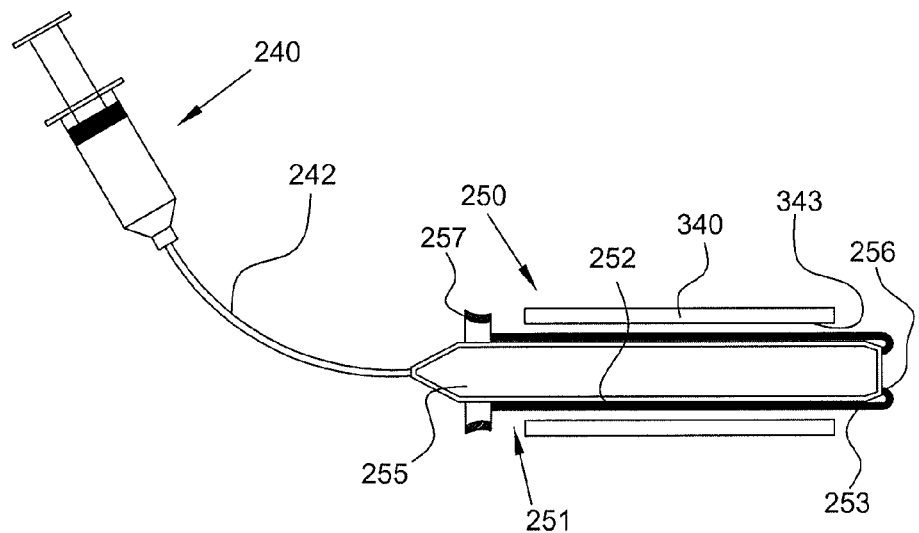
FIG. 6A illustrates side sectional view of an expandable mandrel including a rolling membrane after insertion into a tubular conduit and in an unexpanded state, consistent with the present inventive concepts.
Figure 6B:
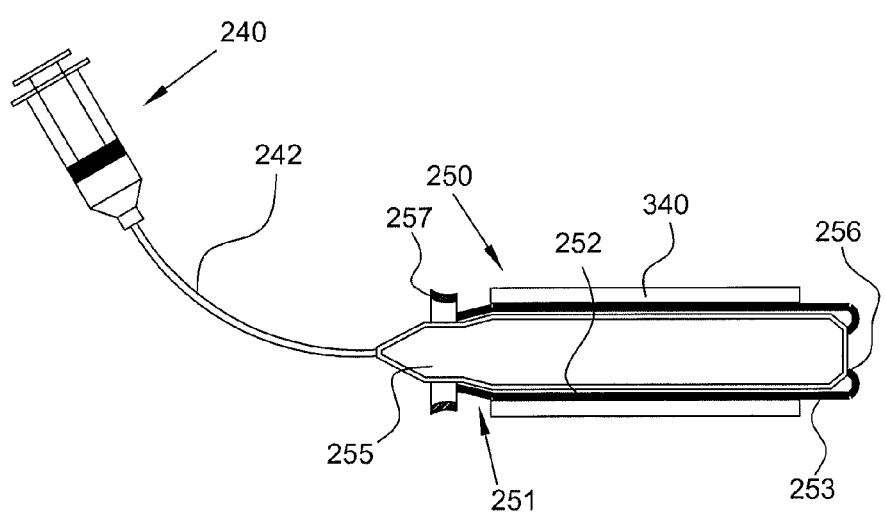
FIG. 6B illustrates a side sectional view of the mandrel of FIG. 6A in an expanded state, consistent with the present inventive concepts.
Figure 7A:
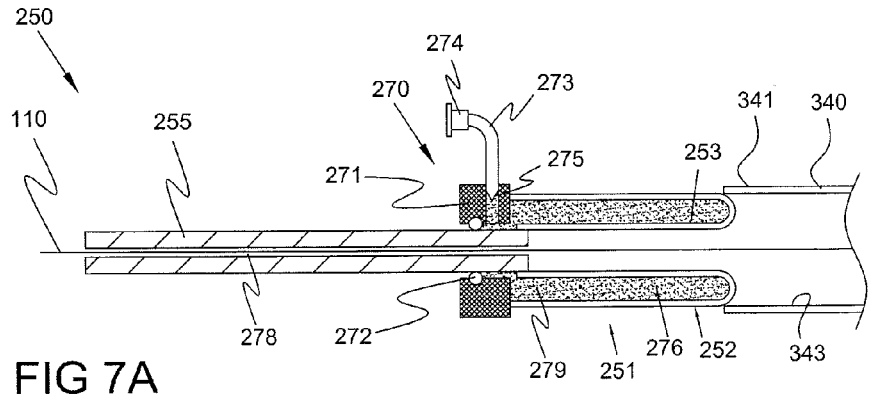
FIGS. 7A-7C illustrate a series of side sectional views an example mandrel being inserted into a tubular conduit, the mandrel including a rolling membrane consistent with the present inventive concepts.
Figure 7B:
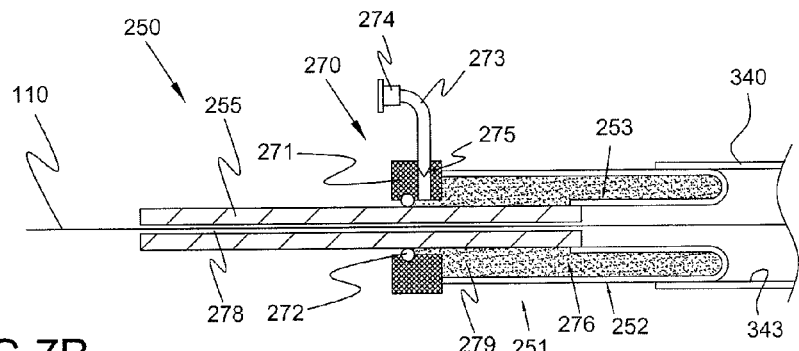
Figure 7C:
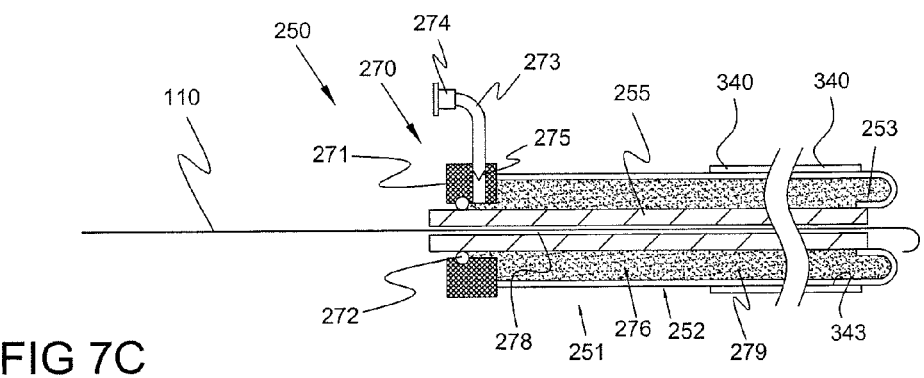

Referring now to FIG. 6A, a side sectional view of a tubular conduit with a pre-inserted mandrel is illustrated, consistent with the present inventive concepts. The mandrel is configured for expansion (shown in an unexpanded state in FIG. 6A) and includes a rolling membrane. Hatching has been removed FIGS. 6A and 6B for illustrative clarity. Mandrel 250 includes a rolling membrane 251, constructed and arranged to minimize trauma to tubular conduit 340 during insertion of mandrel 250 into tubular conduit 340. Tubular conduit 340 can comprise one or more segments of living and/or artificial tissue, as has been described hereabove. Mandrel 250 is constructed and arranged similar to the mandrel of FIGS. 1A-1D, including a similar collar 257. Mandrel 250 is shown positioned within tubular conduit 340, such as after an insertion method, as is described in reference to FIGS. 1A-1D hereabove, except that engagement of mandrel 250 with tubular conduit 340 is accomplished in two steps, or two sets of steps. First, membrane 251 is rollingly unfurled as inserted into tubular conduit 340 as is shown in FIG. 6A. Then mandrel 250 is radially expanded to make contact with inner wall 343 of conduit 340, as shown in FIG. 6B. In some embodiments, as depicted in FIGS. 6A-6B, membrane 251 and shaft 255 are configured to be expanded, such as when shaft 255 comprises a balloon, not shown. Alternatively, shaft 255 can be radially expanded via other means, such as by being twisted when shaft 255 comprises a rolled sheet of material. In FIG. 6A, membrane 251 and shaft 255 are in an unexpanded state, which is typically maintained during the inserting of mandrel 250 into conduit 340.

In FIG. 6B, a fluid such as a gas or a liquid, has been injected into shaft 255 via syringe 240 and tubing 242. Shaft 255 and membrane 251 have been expanded to contact the inner walls 343 of conduit 340. Expansion of mandrel 250 via syringe 240 can be performed without applying sliding, twisting or other traumatic forces to conduit 340. Application of a fiber matrix, such as via the fiber matrix delivery assembly of FIG. 8, is performed with mandrel 250 in an expanded state. After fiber matrix application, mandrel 250 can be deflated (unexpanded), and removed, such as by using the removal method described in reference to FIGS. 2A-2D hereabove.

Referring now to FIGS. 7A-7C, a series of steps for inserting a pressurized mandrel into a tubular conduit are illustrated, consistent with the present inventive concepts. The mandrel of FIGS. 7A-7C includes a pressurization assembly constructed and arranged to provide structural support to a rolling membrane, as the membrane folds over onto itself, such as when it is inserted into and/or removed from a tubular conduit. Mandrel 250 includes a rolling membrane 251, constructed and arranged to limit (e.g., minimize) trauma to tubular conduit 340 during insertion of mandrel 250 into tubular conduit 340.

Mandrel 250 of FIGS. 7A-7C includes similar functionality and components as mandrel 250 of FIGS. 1A-1D, such as a similar membrane 251 including first surface 252 and second surface 253, with similar attachment of membrane 251 to shaft 255 and collar 271. Shaft 255 typically comprises a length as described in reference to FIGS. 1A-1D hereabove, and can be sized to one or more tubular segments, such as one or more harvested segments of a saphenous vein. Shaft 255 includes a lumen 278, such as a lumen configured for insertion of a guidewire such as a J-tipped guidewire 110 configured to aid in atraumatic insertion of mandrel 250 into tubular conduit 340. Shaft 255 can include a taper, not shown but described hereabove in reference to FIGS. 1A-1D. Shaft 255 can be rigid, flexible, or include both rigid and flexible portions. Shaft 255 can be configured to transition to a rigid state, such as the expanding shaft of FIGS. 6A-6B described hereabove.

Mandrel 250 includes a pressurizing assembly 270 which includes sealing collar 271 and an O-ring 272. O-ring 272 slidingly receives shaft 255, and creates a relative fluid seal between shaft 255 and collar 271. O-ring 272 can be hydrophilic, hydrophobic and/or include a hydrophilic, hydrophobic and/or lubricous coating. Shaft 255 is attached at its distal end to the distal portion of rolling membrane 251, as described hereabove. The proximal portion of rolling membrane 251 is fixedly attached to collar 271 as shown, forming a relatively sealed area 276 between surface 253 of rolling membrane 251, shaft 255, O-ring 272 and collar 271. A luer 274 is fluidly attached to tubing 273 which is in turn fluidly attached to a valved chamber 275 of collar 271. Valve chamber 275 can include a valve selected from the group consisting of: a one way valve; a pressure relief valve; a mechanically activated valve; and combinations of these. Valved chamber 275 is in fluid communication with area 276 such that a fluid delivery device, not shown but typically a syringe, pump and/or other positive pressure source, can be used to deliver a pressurization fluid 279 into area 276. Pressurization fluid 279 typically comprises a fluid such as a liquid such as saline, and/or a gas such as air or carbon dioxide. Introduction of pressurization fluid 279 into area 276 provides pressurization forces which cause membrane 251 to have sufficient column strength or other structural supporting forces to maintain the tubular structure shown, such as while folding over during insertion into and/or removal from, tubular conduit 340.

Referring specifically to FIG. 7A, the distal end of mandrel 250 is positioned proximate tubular conduit 340, such that an initial segment of the first surface 252 facing outward is proximate end 341 of conduit 340. Area 276 can be fully or partially pressurized, such as to allow membrane 251 to assume a self-supported elongate profile. In FIG. 7B, shaft 255 is partially advanced, while collar 271 is held in place, such as by the hands of an operator or a tool being controlled by an operator, hands or tools not shown. The pressure within area 276 can be adjusted during this process, such as an adjustment comprising an increase or decrease to the pressure within area 276. Valve chamber 275 can be configured to dynamically release pressuring fluid contained within area 276 as shaft 255 fills the area previously occupied by area 276, such as to avoid over-pressurization of area 276. During this advancement process, additional segments of first surface 252 have folded over while atraumatically engaging inner surface 343 of conduit 340. This engagement comprises a rolling engagement of first surface 252 with inner surface 343, avoiding creation of sliding, twisting and/or other frictional forces that may cause trauma to conduit 340.

In FIG. 7C, shaft 255 has been fully advanced, while collar 271 has been maintained in place as described above. The majority of the length of first surface 252 has folded over while rollingly engaging the inner surface 343 of conduit 340. The majority of second surface 253 now opposes shaft 255, such that less support is derived from the outward pressure provided within area 276 by fluid 279 as was needed in previous stages to maintain the tubular geometry of membrane 251. Final internal pressure of area 276 can be adjusted before mandrel 250 and tubular conduit 340 are inserted into a fiber matrix delivery assembly, such as the electrospinning unit described in reference to FIG. 8 herebelow. Tubing 273 can be removably attached to valve chamber 275, such that tubing 273 can be removed before an electrospinning process is performed.

After fiber matrix application, such as is described in reference to FIG. 8 herebelow, mandrel 250 can be removed, such as by using the removal method described in reference to FIGS. 2A-2D hereabove. Valve 275 can be de-activated and/or otherwise configured to allow a volume of fluid 279 to exit pressurization area 276 during retraction of mandrel 250 from conduit 340.

Referring now to FIG. 8, a side view of an apparatus for producing a graft device is illustrated. Apparatus 10 includes electrospinning unit 400 and mandrel 250. Mandrel 250 comprises a rolling membrane 251, as has been described above in numerous configurations. Conduit 340 has been placed around mandrel 250, such as is described in reference to FIGS. 1A-1D hereabove. Conduit 340 can include living tissue and/or artificial materials, as is described herein. Electrospinning unit 400 can include one or more nozzle assemblies, and in the illustrated embodiment, unit 400 includes nozzle assemblies 405 and 505, which includes nozzles 427 and 527, respectively. For clarification, any reference to a "nozzle" and "nozzle assembly" in singular or plural form can include one or more nozzles, such as nozzles 427 and 527 and one or more nozzle assemblies, such as nozzle assemblies 405 and 505. In one non-limiting embodiment, nozzle 427 can deliver a polymer solution while nozzle 527 can deliver an adhesive layer, such as an adhesive layer configured to limit (e.g., prevent) relative motion between one or more portions of conduit 340 and fiber matrix 320. In some embodiments, nozzle 427 delivers both fibers and adhesive, simultaneously or sequentially, avoiding the need for nozzle 527 or making nozzle 527 available for the delivery of another solution or compound, for example, a drug or an agent. Typically, the polymer solution includes one or more polymers and one or more solvents. Polymers can be selected from the group consisting of: polyolefins; polyurethanes; polyvinylchlorides; polyamides; polyimides; polyacrylates; polyphenolics; polystyrene; polycaprolactone; polylactic acid; polyglycolic acid; and combinations of these. Solvents can be selected from the group consisting of: hexafluoroisopropanol; acetone; methyl ethyl ketone; benzene; toluene; xylene; dimethyleformamide; dimethylacetamide; propanol; ethanol; methanol; propylene glycol; ethylene glycol; trichloroethane; trichloroethylene; carbon tetrachloride; tetrahydrofuran; cyclohexone; cyclohexpropylene glycol; DMSO; tetrahydrofuran; chloroform; methylene chloride; and combinations of these.

In some embodiments, electrospinning unit 400 can be configured to deliver the fiber matrix and/or an adhesive layer according to set parameters. For example, an adhesive layer can be delivered to conduit 340 for a particular length of time, followed by delivery of a polymer solution for another particular length of time. Other examples of application parameters include but are not limited to: amount of adhesive layer and/or polymer solution delivered; rate of adhesive layer and/or polymer solution delivered; nozzle distance to mandrel 250 and/or conduit 340; linear travel distance of a nozzle along its respective drive assembly (for example, drive assembly 445a and 445b); linear travel speed of a nozzle along its respective drive assembly; compositions of the polymer solution and/or adhesive layer; concentrations of the polymer solution and/or adhesive layer; solvent compositions and/or concentrations; fiber matrix inner and outer layer compositions and/or concentrations; spontaneous or sequential delivery of the polymer solution and the adhesive layer; voltage applied to the nozzle; voltage applied to the mandrel; viscosity of the polymer solution; temperature of the treatment environment; relative humidity of the treatment environment; airflow within the treatment environment; and combinations of these.

Nozzles 427 and 527 can be constructed of stainless steel. In some embodiments, nozzles 427 and/or 527 have a tubular construction with a length of approximately 1.5", an ID of approximately 0.047" and an OD of approximately 0.065". Nozzles 427 and 527 can include an insulating coating, with the tip of nozzles 427 and/or 527 exposed (e.g. non-insulated), such as with an exposed length of approximately 1 cm. Nozzle geometry and electrical potential voltages applied between nozzles 427 and/or 527 and mandrel 250 are chosen to control fiber generation. In some embodiments, fibers are created with a diameter between 0.1 µm and 2.0 µm, for example with a diameter between 0.1 µm and 1.0 µm.

Mandrel 250 is positioned in a particular spaced relationship from nozzle assemblies 405 and/or 505 and nozzles 427 and/or 527, respectively. In the illustrated embodiment, mandrel 250 is positioned above and below nozzle assemblies 405 and 505. Alternatively, mandrel 250 can be positioned either above or below the nozzle assemblies 405 and/or 505. In some embodiments, mandrel 250 is located to the right or left of the nozzle assemblies 405 and 505, or both left and right. The distance between mandrel 250 and the tip of nozzles 427 and 527 is can be less than 20 cm, for example less than 15 cm. In a particular embodiment, the tip of nozzles 427 and/or 527 is approximately 12.5 cm from mandrel 250. As illustrated, multiple nozzles 427 and 527, for example nozzles of similar or dissimilar configurations, can be positioned in various orientations relative to mandrel 250. In some embodiments, the distance between nozzles 427 and/or 527 and mandrel 250 and/or conduit 340 varies such that the adhesive layer and polymer solution display various properties, for example, wetness of the adhesive layer and/or the fiber matrix layer. For example, nozzles 427 and/or 527 distance can vary continuously during the electrospinning process or can vary for a set period of time during the process.

An electrical potential can be applied between nozzles 427 and/or 527 and one or both of conduit 340 and mandrel 250. The electrical potential can draw at least one fiber from nozzle assemblies 405 and/or 505 to conduit 340. Conduit 340 can act as the substrate for the electrospinning process, collecting the fibers that are drawn from nozzle assemblies 405 and/or 505 by the electrical potential. In some embodiments, mandrel 250 and/or conduit 340 has a lower voltage than nozzles 427 and/or 527 to create the desired electrical potential. For example, the voltage of mandrel 250 and/or conduit 340 can be a negative or zero voltage while the voltage of nozzles 427 and/or 527 can be a positive voltage. Mandrel 250 and/or conduit 340 can have a voltage of about −5 kV (e.g., −10 kV, −9 kV, −8 kV, −7 kV, −6 kV, −5 kV, −4.5 kV −4 kV, −3.5 kV, −3.0 kV, −2.5 kV, −2 kV, −1.5 kV, −1 kV) and the nozzle 105 can have a voltage of about +15 kV (e.g., 2.5 kV, 5 kV, 7.5 kV, 12 kV, 13.5 kV, 15 kV, 20 kV). In some embodiments, the potential difference between nozzles 427 and/or 527 and mandrel 250 and/or conduit 340 can be from about 5 kV to about 30 kV. This potential difference draws fibers from nozzles 427 and/or 527 to conduit 340. In some embodiments, nozzle 427 and/or 527 is placed at a potential of +15 kV while mandrel 250 is placed at a potential of −5 kV. In some embodiments, mandrel 250 is a fluid mandrel, such as the fluid mandrel described in applicant's co-pending International Patent Application Serial Number PCT/US2011/66905 filed on Dec. 22, 2011, which is incorporated by reference in its entirety.

In some embodiments, a polymer solution, stored in polymer solution dispenser 420, can be delivered to nozzle assembly 405 through a polymer solution delivery tube 425. The electrical potential between nozzle 427 and conduit 340 and/or mandrel 250 can draw the polymer solution through nozzle 427 of nozzle assembly 405. Electrostatic repulsion, caused by the fluid becoming charged from the electrical potential, counteracts the surface tension of a stream of the polymer solution at nozzle 427 of the nozzle assembly 405. After the stream of polymer solution is stretched to its critical point, one or more streams of polymer solution emerges from nozzle 427 of nozzle assembly 405, and/or at a location below nozzle assembly 405, and move toward the negatively charged conduit 340. Using a volatile solvent, the solution dries substantially during transit and the fiber is deposited on conduit 340. Similarly, a solution comprising an adhesive, stored in adhesive solution dispenser 520, can be delivered to nozzle assembly 505 through adhesive solution delivery tube 525 via electrostatic repulsion. In some embodiments, adhesive solution can be delivered via assembly 405, and polymer solution can be delivered via assembly 505. Alternatively or additionally, an adhesive is provided in dispenser 420, such that it can be delivered through nozzle assembly 427. Delivery of the adhesive can be simultaneous with polymer fiber delivery (e.g. when the adhesive is mixed with polymer solution in dispenser 420), or sequential with polymer fiber delivery (e.g. when the adhesive is provided separate from the polymer solution in dispenser 420).

Mandrel 250 is configured to rotate about an axis, such as axis 435, with nozzles 427 and/or 527 perpendicular to axis 435. The rotation around axis 435 allows the fiber matrix to be deposited along all sides, or around the entire circumference of conduit 340. Mandrel 250 can be rotated by at least one motor 440*a*, 440*b* in direct or indirect communication with the ends of mandrel 250. In some embodiments, electrospinning unit 400 includes a single motor that rotates one end of mandrel 250. In some embodiments, two motors 440*a* and 440*b* are used. For example, motor 440*a* can be in communication with one end of mandrel 250 while motor 440*b* is in communication with the opposite end of mandrel 250. The rate of rotation of mandrel 250 can depend on how the fiber matrix is to be applied to conduit 340. For example, for a thicker fiber matrix, the rotation rate can be slower than if a thinner fiber matrix is desired.

In addition to mandrel 250 rotating around axis 435, the nozzle assembly 405 can move, such as when driven by drive assembly 445*a* in a reciprocating or oscillating horizontal motion. Drive assemblies 445*a* and/or 445*b* comprise a linear drive assembly, not shown but typically a belt driven drive assembly comprising two or more pulleys driven by one or more stepper motors. Additionally or alternatively, nozzle assemblies 405 and/or 505 can be constructed and arranged to rotate around axis 435, rotating means not shown. The length of drive assemblies 445*a* and/or 445*b* and the linear motion applied to nozzle assemblies 405 and 505, respectively, can vary based on the length of conduit 340 to which a fiber matrix and/or adhesive layer will be delivered. For example, the supported linear motion of drive assemblies 445*a* and/or 445*b* can be about 10 cm to about 50 cm. Nozzle assemblies 405 and/or 505 can move along drive assemblies 445*a* and/or 445*b*, respectively, to apply a fiber matrix and/or adhesive layer to the entire length, or specific portions of a length, of conduit 340. In some embodiments, fiber(s) and/or adhesive is applied to the entire length of conduit 340 plus an additional 5 cm (to mandrel 250) on either end of conduit 340. In some other embodiments, fiber(s) and/or adhesive is applied to the entire length of conduit 340 plus at least 1 cm beyond either end of conduit 340.

Nozzle assemblies 405 and/or 505 can be controlled such that specific portions along the length of conduit 340 are reinforced with a greater amount of fiber matrix as compared to other or remaining portions. In addition, conduit 340 can be rotating around axis 435 while nozzle assemblies 405 and/or 505 is moving along drive assemblies 445*a* and/or 445*b*, respectively, to provide control over the location on conduit 340 where the fiber matrix will be applied. In some embodiments, nozzle assemblies 405 and/or 505 are translated back and forth at a velocity of approximately 200 mm/sec. Rotational speeds of mandrel 250 and translational speeds of nozzle assemblies 405 and/or 505 can be relatively constant, or can be variable during the process.

Apparatus 10 can also include a power supply, not shown but configured to provide the electric potentials to nozzles 427 and/or 527 and mandrel 250, as well as supply power to other components of apparatus 10 such as drive assemblies 445*a* and 445*b*. The power supply can be connected, either directly or indirectly, to at least one of mandrel 250 and conduit 340. Power can be transferred from the power supply to mandrel 250 and/or conduit 340 by, for example, a wire.

Apparatus 10 can also include inlet and/or outlet ports, not shown, but typically configured to control the environment surrounding nozzles 427 and/or 527 and/or the environment surrounding mandrel 250. A port can be configured to be both an inlet port and an outlet port. Apparatus 10 can include a housing, also not shown, but typically attachable to electrospinning unit 400 and defining a chamber surrounding nozzles 427 and/or 527 and/or mandrel 250, such that the ports can control a more limited (smaller) environment surrounding nozzles 427 and/or 527 and/or mandrel 250. Additionally or alternatively, the ports can be used to introduce or remove one or more gases, introduce or remove humidity, control temperature, control sterility, provide other environmental controls, and combinations of these.

The mandrels discussed herein can assume numerous geometries, such as geometries which include one or more ends with a reduced diameter, a taper, a bevel, or rounded edge, or other atraumatic feature. The mandrels can be configured to be expanded, such as a radial expansion to a diameter less than, approximately equal to, or greater than a relaxed diameter of a vein graft or other tubular conduit. The mandrel can be expanded along a majority of its length, or just a portion. One or more fluids can be delivered, along the full or partial length of the mandrel. Alternatively or additionally, one or more separate devices can be included, such as devices configured to assist in mandrel insertion or removal from a tubular conduit. Mandrels can include one or more coatings, such as a lubricious coating, along the full or partial length of the mandrel. Mandrels can include a lumen, such as a lumen configured to slidingly receive a shaft such as a guidewire shaft, and/or a lumen configured to deliver fluids. Mandrels can include an integral guidewire positioned at one or both ends, such as a guidewire comprising a J-tip configured for atraumatic insertion into a blood vessel of a patient.

While the certain example embodiments of the devices and methods have been described in reference to the environment in which they were developed, they are merely illustrative of the principles of the inventive concepts described herein. Modification or combinations of the above-described assemblies, other embodiments, configurations, and methods, and variations of aspects of the systems and methods described herein that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A system for applying a fiber matrix onto a tubular conduit, the system comprising:
    a tubular conduit comprising an inner surface and an outer surface;
    a mandrel comprising an elongate shaft and a rolling membrane; and
    a fiber matrix delivery assembly, wherein the fiber matrix delivery assembly is constructed and arranged to receive the mandrel and to apply a fiber matrix to the outer surface of the tubular conduit.

2. The system of claim 1 wherein the mandrel is constructed and arranged such that advancement of the elongate shaft causes the rolling membrane to engage with the tubular conduit inner surface.

3. The system of claim 1 wherein the mandrel is constructed and arranged such that advancement of the elongate shaft causes the rolling membrane to fold over onto itself.

4. The system of claim 3 wherein the elongate shaft comprises an expandable shaft and wherein the mandrel is constructed and arranged such that expansion of the elongate shaft causes the rolling membrane to engage with the tubular conduit inner surface.

5. The system of claim 1 wherein the mandrel is constructed and arranged such that retraction of the elongate shaft disengages the rolling membrane with the inner surface of the tubular conduit.

6. The system of claim 1 wherein the mandrel comprises a relatively straight mandrel.

7. The system of claim 1 wherein the mandrel comprises at least one curved portion.

8. The system of claim 1 wherein the mandrel comprises a lumen.

9. The system of claim 1 wherein the mandrel comprises a distal end and a guidewire extending from said distal end.

10. The system of claim 1 wherein the rolling membrane comprises a material selected from the group consisting of: polyester, polyamide, polyethylene terephthalate, crosslinked polyethylene, polyurethane, polyvinylchloride, polytetrafluoroethylene, nylon, polyether block amides, silicone, polyether, and any combinations thereof.

11. The system of claim 1 further comprising at least one axial stiffener positioned on and/or within the rolling membrane.

12. The system of claim 11 wherein the at least one axial stiffener is constructed and arranged to reduce a motion of the rolling membrane selected from the group consisting of: twisting; folding; collapsing; and combinations thereof.

13. The system of claim 1 further comprising a pressurization assembly comprising a pressurization area, said pressurization area constructed and arranged to provide axial support to the rolling membrane as the rolling membrane folds over onto itself.

14. The system of claim 1 wherein the rolling membrane comprises a conductive membrane.

15. The system of claim 1 wherein the rolling membrane comprises at least one porous portion.

16. The system of claim 15, further comprising a fluid delivered to the tubular conduit via the rolling membrane and arranged to perform a function selected from the group consisting of: hydrate the tubular conduit;
    deliver one or more drugs, cells or other agents to the tubular conduit; modify the tubular conduit; cool or warm the tubular conduit; and combinations thereof.

17. The system of claim 1 wherein the elongate shaft comprises an expandable shaft.

18. The system of claim 1 wherein the elongate shaft comprises at least one tapered end.

19. The system of claim 1 wherein the fiber matrix delivery assembly comprises a device selected from the group consisting of: electrospinning unit; misting assembly; sipping assembly; sprayer; braiding device; micropatterning device; injection device; and combinations thereof.

20. The system of claim 1 wherein the tubular conduit comprises a living tissue selected from the group consisting of: vein; saphenous vein; artery; lymphatic duct; vas deferens; tear duct; intestine; esophagus; ureter; urethra; trachea; bronchi; duct tissue; Eustachian tube; fallopian tube; and combinations thereof.

* * * * *